(12) United States Patent
Rodriguez (10) Patent No.: US 9,549,816 B2
(45) Date of Patent: Jan. 24, 2017

(54) METHOD FOR MANUFACTURING HIGH DURABILITY HEART VALVE

(71) Applicant: Edwards Lifesciences Corporation, Irvine, CA (US)

(72) Inventor: Rodolfo Rodriguez, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 14/677,746

(22) Filed: Apr. 2, 2015

(65) Prior Publication Data

US 2015/0282929 A1 Oct. 8, 2015

Related U.S. Application Data

(60) Provisional application No. 61/974,943, filed on Apr. 3, 2014.

(51) Int. Cl.
*A61F 2/24* (2006.01)
*C23C 14/06* (2006.01)
(Continued)

(52) U.S. Cl.
CPC ............. *A61F 2/2415* (2013.01); *A61F 2/24* (2013.01); *A61F 2/2418* (2013.01);
(Continued)

(58) Field of Classification Search
CPC ................... Y10T 29/49982; Y10T 29/49885; A61F 2/2412; A61F 2/24; C23C 14/24; C23C 14/0641
See application file for complete search history.

(56) References Cited

U.S. PATENT DOCUMENTS 3,143,742 A   8/1964   Cromie
3,320,972 A   5/1967   High et al.
(Continued)

FOREIGN PATENT DOCUMENTS

EP   0125393 A1   11/1984
EP   0143246 A2   6/1985
(Continued)

OTHER PUBLICATIONS

Liu, H. et al, "Mechanical Property and Rolling Contact Fatigue Life of TiN Film on Bearing Steel by Plasma Immersion Ion Implantation and Deposition," Reviews on Advance Material Science, 2013, vol. 33, pp. 131-136.

*Primary Examiner* — Jermie Cozart
(74) *Attorney, Agent, or Firm* — Guy Cumberbatch; Pui Tong Ho (57) ABSTRACT

An improved heart bioprosthetic device having a metal frame wireform or stent having an outer external surface. The metal frame has a bond layer coating at least a portion of the external surface and a coating layer disposed on at least a portion of the bond layer. The bond layer comprises a metal selected from the group consisting of: chromium, titanium, zirconium, aluminum, platinum, palladium, and niobium. The coating layer is selected from the group consisting of: a metal nitride, a metal oxide, a metal carbide, and combinations thereof. The coating layer may have a thickness of about 10 μm or less and a grain size of about 10 nm to about 15 nm, and may be characterized as polycrystalline with randomly-oriented grains with both cubic and orthorhombic phases. In one embodiment, the bond layer comprises chromium and the coating layer comprises chromium nitride.

25 Claims, 3 Drawing Sheets

(51) Int. Cl.
   *C23C 14/24* (2006.01)
   *C23C 14/32* (2006.01)
   *C23C 16/34* (2006.01)
   *C23C 16/44* (2006.01)
   *C23C 14/02* (2006.01)

(52) U.S. Cl.
   CPC ........ *C23C 14/025* (2013.01); *C23C 14/0641* (2013.01); *C23C 14/24* (2013.01); *C23C 14/325* (2013.01); *C23C 16/34* (2013.01); *C23C 16/44* (2013.01); *A61F 2/2412* (2013.01); *Y10T 29/49885* (2015.01); *Y10T 29/49982* (2015.01)

(56) References Cited

U.S. PATENT DOCUMENTS

| | | |
|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,822,355 A * | 4/1989 | Bhuvaneshwar ..... A61F 2/2406 623/2.25 |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,496,359 A | 3/1996 | Davidson |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,171,335 B1 | 1/2001 | Wheatley et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |

(56) References Cited

U.S. PATENT DOCUMENTS

| | | |
|---|---|---|
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,387,121 B1 | 5/2002 | Alt |
| 6,402,780 B2 | 6/2002 | Williamson, IV et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,761,736 B1 | 7/2004 | Woo |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,582,112 B2 * | 9/2009 | Scheuermann .......... A61F 2/91 623/1.46 |
| 7,632,309 B1 * | 12/2009 | Brendzel .............. A61F 2/0077 623/2.42 |
| 7,998,151 B2 | 8/2011 | St. Goar et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 * | 12/2002 | Schreck .............. A61F 2/2418 623/2.11 |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |

(56) References Cited

U.S. PATENT DOCUMENTS

| | | |
|---|---|---|
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0154356 A1 | 6/2008 | Obermiller et al. |
| 2008/0215144 A1* | 9/2008 | Ryan ................... A61F 2/2418 623/2.18 |
| 2008/0319543 A1 | 12/2008 | Lane |
| 2009/0036903 A1 | 2/2009 | Ino et al. |
| 2009/0192599 A1 | 7/2009 | Lane et al. |
| 2010/0049313 A1 | 2/2010 | Alon et al. |
| 2013/0211310 A1* | 8/2013 | Bommarito ............ B08B 17/06 602/48 |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |
| WO | 2012000401 A1 | 1/2012 |

* cited by examiner

METHOD FOR MANUFACTURING HIGH DURABILITY HEART VALVE

CROSS-REFERENCE TO RELATED APPLICATIONS

This application claims the benefit of U.S. patent application No. 61/974,943, filed Apr. 3, 2014, the entire disclosure of which is incorporated by reference in its entirety.

TECHNICAL FIELD

The invention relates to a method of treating a metal substrate to increase its durability and, more particularly, to a method of coating heart valve frames, such as wireforms and stents, to increase the fatigue life.

BACKGROUND

Heart valves are dynamic structures that experience constant and cyclic mechanical stress from the hemodynamic forces intrinsic to its function. When the function of a natural heart valve declines or fails, replacement is typically required with a bioprosthetic heart valve.

One common type of bioprosthetic heart valve is a biological tissue valve, which is usually coupled to and supported by a metal frame. The metal frame can be either a wireform or a collapsible/expandable stent. Once implanted, the bioprosthetic heart valve is subjected to cyclic hemodynamic forces, causing the leaflets to open and coapt. These forces, in turn, impart mechanical stresses onto the supporting metal frame. It is therefore desirable for the metal frame to have a structural integrity that is capable of withstanding these stresses.

The surface of a metal frame, such as a wireform or stent, may often be riddled with small imperfections that can ultimately lead to reduced fatigue life and premature failure. These flaws can be in the form of inclusions (particles), draw lines, knit lines, or scratches, which are introduced during the manufacture of the wire or tube used to form the wireform or stent, respectively. It is therefore desirable to remove or ameliorate these imperfections before incorporating the metal frame into a heart valve.

One method of addressing the surface imperfections of the metal frame is to mechanically polish the surface. It is difficult, however, to mechanically polish the surface of a metal frame because the surface is not flat and typically has intricate or curved geometric configurations. It would be prohibitively difficult to uniformly polish the surface of the shaped metal frame. A similar challenge is presented with respect to electropolishing. Additionally, while mechanical polishing or electropolishing may remove certain imperfections, they may expose certain other imperfections existing below the surface of the metal frame.

What is therefore needed is a method for treating a metal frame of a bioprosthetic heart valve to improve its fatigue life, and thus, durability once implanted in a patient.

BRIEF SUMMARY

Methods and bioprosthetic heart valves comprising metal frames are disclosed in which the metal frames may be subjected to further treatment to coat at least a portion of, if not the entirety of, the external surface with a bond layer and a coating layer, to thereby increase its fatigue life and durability once implanted in a patient. The methods described herein are particularly advantageous in allowing for a uniform application of a coating layer despite the curved, rounded, or otherwise intricate geometries of the metal frames that constitute a bioprosthetic heart valve. Moreover, process parameters for the application of the bond and coating layers may be tailored so as to not disturb the properties or the shape of the metal frame.

In one embodiment, a method for improving the fatigue life of a metal substrate is described. The method may comprise providing a metal frame, such as a stent or a wireform. The method may further comprise applying a bond layer to at least a portion of an external surface of the metal frame. The method may further comprise applying a coating material to at least a portion of the bond layer disposed on the external surface of the metal frame using a technique selected from the group consisting of: physical vapor deposition (PVD) and chemical vapor deposition (CVD). The coating may be applied at a temperature of about 150° C. (about 300° F.) or less. The coating layer may have a thickness of 10 µm or less.

In accordance with a first separate aspect, the metal frame may be made of a material selected from the group consisting of: a metal alloy, a shape-memory metal and a superelastic metal.

In accordance with a second separate aspect, the PVD may be a low-temperature arc-vapor deposition (LTAVD).

In accordance with a third separate aspect, the coating may be applied at a temperature of about 145° C. (about 296° F.).

In accordance with a fourth separate aspect, the bond layer may comprise one or a combination selected from the group consisting of: chromium, titanium, zirconium, aluminum, platinum, palladium, and niobium.

In accordance with a fifth separate aspect, the bond layer and the coating material may comprise the same metal.

In accordance with a sixth separate aspect, the coating material may be made of one or a combination of materials selected from the group consisting of: a metal oxide, a metal nitride, and a metal carbide.

In accordance with a seventh separate aspect, the metal of the metal oxide, the metal nitride, or the metal carbide may be one or more selected from the group consisting of: chromium, titanium, zirconium, aluminum, platinum, palladium, and niobium.

In accordance with an eighth separate aspect, the coating material may be made of chromium nitride.

In accordance with a ninth separate aspect, the coating with the chromium nitride may be performed using LTAVD.

In accordance with a tenth separate aspect, the coating layer may have a thickness of about 5 µm or less. The coating layer may have a thickness about 1 µm or less.

In another embodiment, an improved bioprosthetic heart valve is provided. The bioprosthetic heart valve may comprise a metal frame and a biological tissue coupled to the metal frame forming leaflets of the heart valve. The metal frame may have an external surface and a bond layer coating at least a portion of the external surface of the metal frame. The bond layer may comprise a metal selected from the group consisting of: chromium, titanium, zirconium, aluminum, platinum, palladium, and niobium. A coating layer may be disposed on at least a portion of the bond layer. The coating layer may be selected from the group consisting of: a metal nitride, a metal oxide, a metal carbide, and combinations thereof.

In accordance with a first separate aspect, the coating layer may have a thickness of about 10 µm or less.

In accordance with a second separate aspect, the coating layer may have a grain size of about 20 nm or less.

In accordance with a third separate aspect, the coating layer may have a grain size of from about 10 nm to about 15 nm.

In accordance with a fourth separate aspect, the coating layer may have both cubic and orthorhombic phases.

In accordance with a fifth separate aspect, the coating layer may be polycrystalline with randomly oriented grains.

In accordance with a sixth separate aspect, the bond layer and the coating layer may comprise the same metal.

In accordance with a seventh separate aspect, the bond layer may comprise chromium.

In accordance with a eighth separate aspect, the coating layer may comprise chromium nitride.

Another embodiment provides a method for improving a fatigue life of a metal frame of an implantable device, the method comprising: disposing a bond layer over at least a portion of a metal frame of an implantable device, the bond layer comprising at least one elemental metal; and vacuum depositing a coating layer over at least a portion of the bond layer, the coating layer comprising at least one of a metal oxide, a metal nitride, or a metal carbide.

In some embodiments, disposing the bond layer comprises disposing a bond layer by at least one of vacuum deposition or by electrochemical deposition. In some embodiments, the at least one elemental metal is selected from the group consisting of aluminum, titanium, zirconium, hafnium, vanadium, niobium, tantalum, chromium, molybdenum, tungsten, ruthenium, cobalt, rhenium, iridium, palladium, platinum, copper, silver, and gold. In some embodiments, disposing the bond layer over at least the portion of the metal frame comprises disposing the bond layer over at least a portion of at least one of a stent or a wireform of a heart valve. In some embodiments, disposing the bond layer over at least the portion of the metal frame comprises disposing the bond layer over at least a portion of a metal frame comprising at least one of stainless steel, cobalt-chromium, titanium alloy, nitinol, a metal alloy, a shape-memory metal, or a super-elastic metal.

In some embodiments, vacuum depositing the coating layer comprises vacuum depositing a coating layer using at least one of physical vapor deposition (PVD), chemical vapor deposition (CVD), or low-temperature arc-vapor deposition (LTAVD). In some embodiments, vacuum depositing the coating layer comprises vacuum depositing the coating layer at a temperature of about 150° C. (about 300° F.) or lower. In some embodiments, vacuum depositing the coating layer comprises vacuum depositing a coating layer with a thickness of about 10 μm or less. In some embodiments, the at least one of the metal oxide, the metal nitride, or the metal carbide of the coating layer comprises at least one metal selected from the group consisting of aluminum, titanium, zirconium, hafnium, vanadium, niobium, tantalum, chromium, molybdenum, tungsten, ruthenium, cobalt, rhenium, iridium, palladium, and platinum.

In some embodiments, vacuum depositing the coating layer comprises vacuum depositing a coating layer comprising chromium nitride. In some embodiments, the bond layer and the coating layer include the same metal.

Another embodiment provides a prosthetic heart valve comprising: a metal frame; a bond layer disposed over at least a portion of the metal frame, the bond layer comprising at least one elemental metal; a coating layer disposed over at least a portion of the bond layer, the coating layer comprising at least one of a metal nitride, a metal oxide, or a metal carbide; and a plurality of leaflets secured to the metal frame, the plurality of leaflets defining a one-way valve for blood flow therethrough.

In some embodiments, the at least one elemental metal of the bond layer includes at least one of aluminum, titanium, zirconium, hafnium, vanadium, niobium, tantalum, chromium, molybdenum, tungsten, ruthenium, cobalt, rhenium, iridium, palladium, platinum, copper, silver, and gold.

In some embodiments, the coating layer has a thickness of about 10 μm or less. In some embodiments, the coating layer has a grain size of about 20 nm or less. In some embodiments, the coating layer includes both cubic and orthorhombic phases. In some embodiments, the coating layer is polycrystalline with randomly oriented grains.

In some embodiments, the at least one of the metal oxide, the metal nitride, or the metal carbide of the coating layer comprises at least one metal selected from the group consisting of aluminum, titanium, zirconium, hafnium, vanadium, niobium, tantalum, chromium, molybdenum, tungsten, ruthenium, cobalt, rhenium, iridium, palladium, and platinum. In some embodiments, the bond layer comprises chromium and the coating layer comprises chromium nitride.

Another embodiment provides a method for manufacturing a prosthetic heart valve, the method comprising: vacuum depositing a coating layer over at least a portion of a metal frame; and securing a plurality of leaflets to the metal frame, the plurality of leaflets defining a one-way valve for blood flow therethrough.

In some embodiments, vacuum depositing the coating layer comprises vacuum depositing the coating layer using at least one of physical vapor deposition (PVD), chemical vapor deposition (CVD), or low-temperature arc-vapor deposition (LTAVD). In some embodiments, wherein vacuum depositing the coating layer comprises vacuum depositing a coating layer comprising at least one of a metal oxide, a metal nitride, or a metal carbide.

Some embodiments further comprise disposing a bond layer over at least a portion of the metal frame, the bond layer comprising at least one elemental metal. In some embodiments, disposing the bond layer comprising at least one of vacuum depositing a bond layer or electrochemically depositing a bond layer.

In some embodiments, securing the plurality of leaflets comprises securing a plurality of tissue leaflets.

It is understood that each one of the separate aspects described above may be optional, may be provided alone, or in combination with any other aspects. Other objects, features, and advantages of the described embodiments will become apparent to those skilled in the art from the following detailed description. It is to be understood, however, that the detailed description and specific examples, while indicating embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which.

Like numerals refer to like parts throughout the several views of the drawings.

DETAILED DESCRIPTION OF CERTAIN EMBODIMENTS

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Embodiments of the structures and methods disclosed herein are useful for a wide variety of implantable devices, and in particular, a device or component that is susceptible to failure from fatigue, for example, one that experiences repeated and/or cyclical loading and unloading. Examples of suitable devices include prosthetic heart valves, stents, annuloplasty rings and bands, and orthopedic and dental implants. Other examples include pacemaker leads and other prosthetics and devices used to treat the heart and/or lungs. The disclosure focuses on prosthetic heart valves, including bioprosthetic heart valves, but the structures and processes apply equally to these and other implantable devices and components.

The bioprosthetic heart valves and the methods disclosed herein provide metal frames, such as wireforms or stents, which may comprise a bond layer and coating layer disposed on at least a portion of the external surface so as to enhance the fatigue life thereof.

Fatigue generally refers to the weakening of a material caused by repeatedly applied loads and the progressive and localized structural damage that can occur when a material is subjected to cyclic loading. Thus, fatigue occurs when a material is subjected to repeated loading and unloading. If the loads are above a certain threshold, microscopic cracks may form and eventually a crack may reach a critical size where it may propagate and cause the structure to fracture. Fatigue life is sometimes defined as the number of stress cycles of a specified character that a specimen sustains before failure of a specified nature occurs.

While metal frames for bioprosthetic heart valves can take on a number of different forms, the most common configurations are wireforms and tubular stents. Some prosthetic valve frames include both a wireform and a stent.

Metal frames of a bioprosthetic heart valve may be subjected to fatigue by the hemodynamic forces that act upon the heart valve after implantation. The metal frames are typically wireforms or stents that may be made of a metal alloy, a shape memory metal, or a super-elastic metal. Examples of suitable metals for frames include steel (for example, stainless steel), nickel-titanium alloys (for example, nitinol), cobalt-chromium alloys (for example, alloys of cobalt, chromium, nickel, iron, molybdenum, and manganese, including Elgiloy® or MP35N™ cobalt-chromium alloys (Elgiloy Specialty Metals, Elgin, Ill.)), and titanium alloys (for example, titanium 6-4). Stents can be laser cut or machined from metal tubes, while wireframes are typically made from metal wire, although other manufacturing methods are also used, for example, 3D-printing, stamping, forging, and the like.

Figure 1:
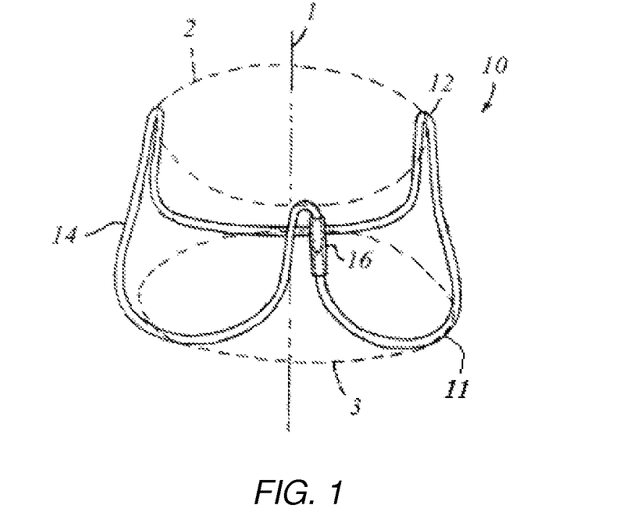
FIG. 1 is a perspective view of a wireform used in the construction of biological tissue heart valves.

FIG. 1 is a perspective view of one example of a wireform frame 10 used in the construction of prosthetic heart valves. The wireform frame 10 includes alternating and oppositely-directed cusps 11 and commissure tips 12. The commissure tips 12 lie in a plane on an imaginary circle 2 about axis 1. Likewise, the apices of the arcuate cusps 11 lie in a plane on an imaginary circle 3 about axis 1. Gradual bends 14 define transitions between the commissure tips 12 and the adjacent cusps 11. A crimp 16 holds together the two free ends of the wire used to form the wireform 10. The crimp 16 is typically a short, tubular metallic member that is compressed about the free ends and holds them by friction. It will thus be understood that the relatively complex contours of the wireform 10 may be controlled to a high degree to result in the desired three-dimensional shape. Leaflets are attached to the wireform frame 10, defining a one-way valve for blood flow therethrough. The example illustrated FIG. 1 includes three commissure tips 12 and cusps, and consequently, accepts three leaflets arranged in a tricuspid configuration. In a bioprosthetic valve, the leaflets are made from tissue or biological material, for example, pericardium, including, for example, bovine, porcine, ovine, equine, or kangaroo pericardium. Other examples use synthetic leaflets, for example, polymer and/or fabric. Other valves have composite leaflets including both tissue and synthetic material.

Figure 2:
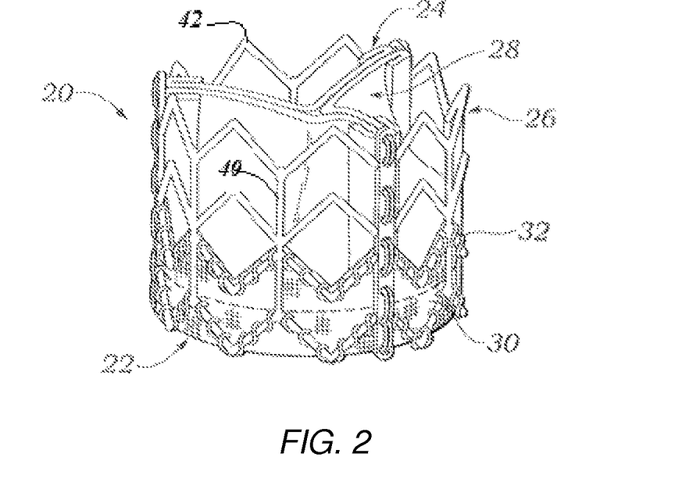
FIG. 2 is a perspective view of a stented biological tissue valve.

FIG. 2 is a perspective view of one example of a stented biological heart valve 20 comprising a biological tissue leaflet structure 28 coupled to a metal stent 26. The leaflet structure 28 and metal stent 26 can be configured to be radially collapsible to a collapsed or crimped state for introduction into the body on a delivery catheter and radially expandable to an expanded state for implanting the valve at a desired location in the body. The valve 20 in the illustrated embodiment further comprises a flexible skirt 30 secured to the outer surface of the leaflet structure 28 and has a lower inflow end 22 and an upper outflow end 24. The skirt 30 can be secured to the inside of the stent 26 via sutures 32. Blood flows upward freely through the valve 20 but the flexible leaflet structure 28 closes to prevent reverse, downward flow. As with the embodiment illustrated in FIG. 1, the leaflets can also be synthetic or composite.

Metal frames for bioprosthetic heart valves, such as the ones depicted and described with respect to FIGS. 1 and 2, can be treated in accordance with the methods of applying a bond layer and coating layer described herein to increase their inherent fatigue life, and thus, providing increased longevity of the implanted valve.

Figure 3:
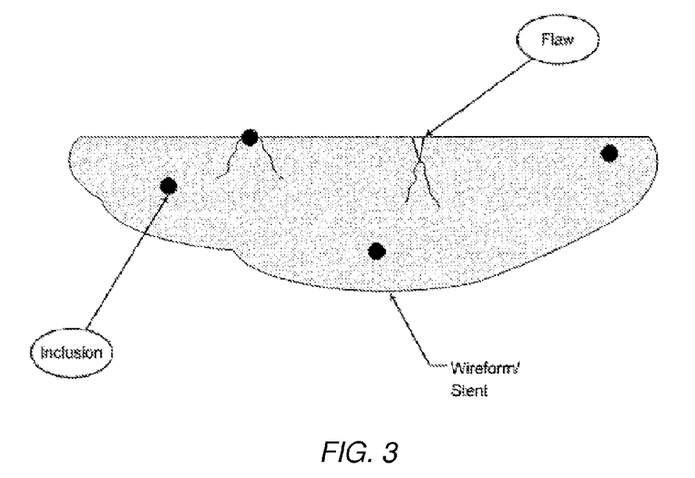
FIG. 3 is a partial cross-sectional view of a metal wireform or stent showing a flaw that is revealed on an external surface of the metal wireform or stent and inclusions and flaws beneath the external surface.

FIG. 3 illustrates the various flaws or defects that can be found both on the surface of and also within the metal wireform or stent that can lead to premature failure and reduced fatigue life. Typical flaws take the form of inclusions (particles), draw lines, knit lines, or scratches that may be introduced to the metal during the manufacture of the wire or tube used in the manufacture the wireforms and stents, respectively. Some of the imperfections can be eliminated by electropolishing the wire or tube, but not all imperfections can be removed and, in some cases, electropolishing can create additional flaws or expose of other imperfections previously disposed under the external surface of the article.

Figure 4:
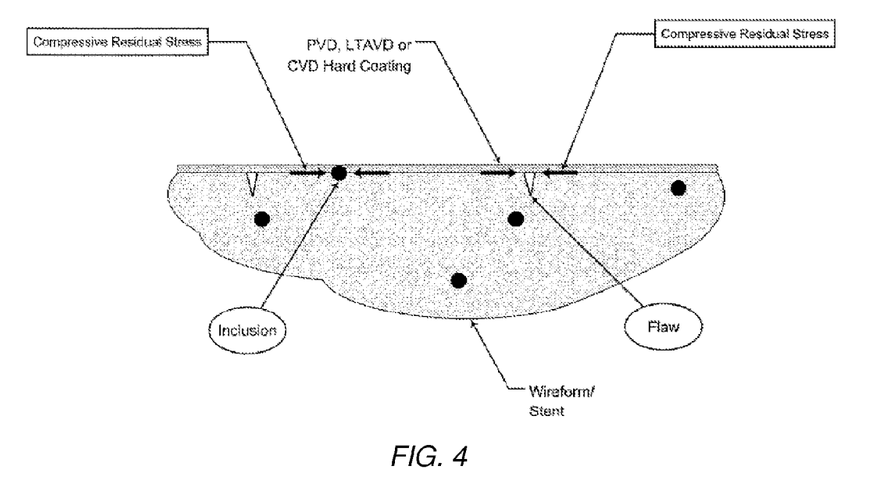
FIG. 4 is a partial cross-sectional view of the metal wireform or stent of FIG. 3 having a bond layer and coating provided on the external surface.

FIG. 4 depicts the surface of the metal wireform or stent having a layer of a hard, wear-resistant coating, e.g., a bond or base layer, and a coating layer in the illustrated embodiment. In some embodiments, the wear-resistant coating covers all or substantially all of the outer surface of the metal frame, while in others, only a portion of the frame, for example, parts, assemblies, or subassemblies that are most susceptible to fatigue.

Some embodiments of the wear-resistant coating do not include a bond layer, while other embodiments include a partial bond layer, that is, a bond layer underlying only a portion of the coating layer. In some cases the bond layer is completely overlaid by the coating layer, while in others, at least a portion of the bond layer remains exposed.

Without being bound by any theory, it is believed that large compressive residual stresses may be generated by the differences in thermal expansion and stiffness between the metal frame and the coatings. This large residual stress lowers the operating stress at the metal frame, instead operating or manifesting at the coating surface, which is generally at least about 3 to 4 times stronger than the substrate.

One or more vacuum deposition processes, for example, physical vapor deposition (PVD), low-temperature arc-vapor deposition (LTAVD), and/or chemical deposition (CVD), can be used to apply each of the bond and coating layers independently onto the external surface of the wireforms and stents to reduce or minimize premature failure and enhance fatigue life. The term "vacuum deposition process" refers generally to deposition processes that are performed under reduced pressure. While the term includes processes that are performed under vacuum, that is, substantially absent any gas pressure, it also includes processes performed in the presence of one or more gases and/or plasma, at a pressure lower than atmospheric pressure.

Physical vapor deposition (PVD) refers to a variety of vacuum deposition methods used to deposit thin films by the condensation of a vaporized form of the desired film material onto various work piece surfaces. The coating method may involve physical processes, such as high-temperature vacuum evaporation with subsequent condensation, or plasma sputter bombardment rather than involving a chemical reaction at the surface to be coated.

Developments in PVD permit vapor-deposited coatings to be applied at relatively lower temperatures. An example of such a technique, known as low-temperature arc-vapor deposition (LTAVD), can be used to apply metals and other materials at low and even at near ambient temperature. Parts to be coated may be placed in a chamber and revolve around a cathode that serves as the metallic source of the coating. A vacuum is drawn on the chamber and a low-voltage arc can be established on the metal source. The arc may evaporate the metal from the source.

The chamber may be charged with at least one or a mixture of inert and reactive gasses, such as argon, helium, and nitrogen, which may form an arc-generated plasma surrounding the source. Arc-evaporated metal atoms and reactive-gas molecules may ionize in the plasma and accelerate away from the source. Arc-generated plasmas are unique in that they may generate a flux of atoms and molecules that have high energies and are mostly (>95%) ionized. The high energy may cause hard and adherent coatings to form on the work piece mounted to one or more fixtures rotating around the source. A bias power supply may be used to apply a negative charge to the parts, which further boosts the energy of the condensing atoms.

Chemical vapor deposition (CVD) is a chemical process that may be used to produce high-purity, high-performance solid materials. In typical CVD, the work piece is exposed to one or more volatile precursors, which react and/or decompose on the substrate surface to produce the desired layer, film, or deposit. Any volatile by-products may be removed by a gas flow or purge through the reaction chamber.

In one embodiment, LTAVD may be utilized to apply both the bond and coating layers onto the metal frame. The use of LTAVD may be advantageous for wireforms and stents as some metals used for the metal frames (e.g., Elgiloy® cobalt-chromium alloy and nitinol) can be sensitive to, and can change properties, when exposed to high temperatures. In particular, higher temperatures can cause a frame to lose temper. A nitinol frame can lose its shape memory at higher temperatures as well. An acceptable temperature that can be used in deposit a coating layer onto any particular frame will depend on factors including the particular composition of the frame, the thermal history of the frame, and/or whether the frame was mechanically or work hardened. For example, in some embodiments the bond and/or coating layers may be applied at a temperature of about 150° C. (about 300° F.) or less, for example, at a temperature of about 145° C. (about 296° F.). Other frames can withstand deposition temperatures up to about 595° C. (about 1100° F.), while in others, the deposition is performed at about 200° C. (about 400° F.) or lower. In some cases, lower temperatures are used with nitinol frames that have been shape-set.

Deposition rates may be from about 0.7 μm to about 1 μm per hour for each layer. The coating layer may have a thickness of about 10 μm or less, a thickness of about 5 μm or less, or a thickness of about 1 μm or less. In some embodiments, the combined bond and coating layers, together, may have a thickness of about 10 μm or less, a thickness of about 5 μm or less, or a thickness of about 1 μm or less.

The deposition of the bond layer by LTAVD in a vacuum chamber may be performed using an inert gas, such as argon or helium. In another embodiment, at least a portion of the bond or base layer is disposed onto the frame by a different method, for example, electrochemically. Embodiments of electrochemical depositions of the bond layer are performed at from about 0° C. to about 100° C., for example, at about ambient temperature. Moreover, however the bond and coating layers are applied, each may independently be subjected to post-application treatment or processing, for example, thermal and/or chemical processing. Chemical processing includes contacting the coating layer with one or more reactive chemical species, for example a gas, plasma, and/or liquid phase reactive species. Particular examples include reduction and oxidation, which can modify either a full or partial thickness of a coating layer.

The bond and coating layers may be applied to the metal frame after it is shaped and/or fabricated, but before it is assembled with the biological tissue to form the final bioprosthetic heart valve. As the metal frame (e.g., the wireform or stent) has a three-dimensional, rounded, or cylindrical geometry, uniform application of the base and coating layers may be achieved by rotating and moving either one or both of the metal frame or metallic source relative to one another. In one embodiment, the metal frame may be coupled to a movable support inside the chamber that may rotate and expose substantially all sides of the metal frame to the plasma so as to provide a uniform coating of the base and coating layers thereon. The support may couple to an area of the metal frame that experiences the least amount of stress or force. For example, for the wireform depicted in FIG. 1, the crimp 16 or the gradual bends 14 typically experiences the least amount of stress and thus may be an ideal location for coupling to the support. For the stent 20 depicted in FIG. 2, this location may be the one of the vertical posts 40 or the apex 42 of the stent.

Without being bound by any theory, it is believe that the bond layer may promote adhesion between the frame and the coating layer, and in some embodiments, may comprise any suitable material that is softer and more compliant than the coating layer. As such, the bond layer can be a thin layer, for example, as thin as from a few to a few tens of atoms thick. Thicker bond layers are used in some cases. Examples of thinner bond layers have thicknesses of from about 3 Å to about 30 Å, or from about 5 Å to about 15 Å. Embodiments of the bond layer are up to about 0.1 µm (100 Å) thick, for example, up to about 50 Å. The bond layer may comprise a stable and non-reactive elemental metal including one or more noble metals. The elemental metal of the bond layer may be biocompatible or non-biocompatible. For example, in embodiments in which the coating layer completely covers the bond layer, no portion of the bond layer is exposed, and as such, biocompatibility is less important. As such, factors including deposition conditions, ease of deposition, reproducibility, compatibility with the coating layer, adhesion of the coating layer, durability of the entire wear-resistant coating, and improvement in fatigue resistance can take precedence in such cases. Some embodiments of the bond layer include a plurality of layers of different materials, for example, for improved lattice matching between the underlying metal frame and the coating layer and/or to encapsulate a less biocompatible metal. Accordingly, the bond layer may comprise any one or a combination of elemental metals selected from aluminum, titanium, zirconium, hafnium, vanadium, niobium, tantalum, chromium, molybdenum, tungsten, ruthenium, cobalt, rhenium, iridium, palladium, platinum, copper, silver, and gold.

The coating layer may comprise one or a combination of materials selected from a metal oxide, a metal nitride, and a metal carbide. In one embodiment, the metal of the metal oxide, the metal nitride, or the metal carbide may comprise one or more of aluminum, titanium, zirconium, hafnium, vanadium, niobium, tantalum, chromium, molybdenum, tungsten, ruthenium, cobalt, rhenium, iridium, palladium, and platinum. The coating layer may be polycrystalline with randomly-oriented grains. The grain size may be about 20 nm or less, or from about 10 nm to about 15 nm. Additionally, the coating layer may further comprise both cubic and orthorhombic phases. Application of the coating layer by LTAVD in a vacuum chamber may be performed with at least one reactive gas selected from the group consisting of $N_2$, $O_2$, $CO_2$, and $CH_4$. Some embodiments use a gas mixture further including at least one inert gas, for example, argon or helium.

In some embodiments, the bond layer and the coating layer may comprise the same metal, which may facilitate manufacture of the wear-resistant coating. For example, after depositing a bond layer by LTAVD using a particular metallic source and an inert gas to generate the plasma, adding an appropriate gas to the reaction chamber, for example, nitrogen, oxygen, or methane, permits depositing a coating layer of the same metal nitride, oxide, or carbide, respectively.

In another embodiment, the bond layer may be chromium and the coating material may be chromium nitride (CrN). Chromium nitride coatings exhibit corrosion resistance, as well as hardness and wear-resistance.

EXAMPLE

Figure 5:
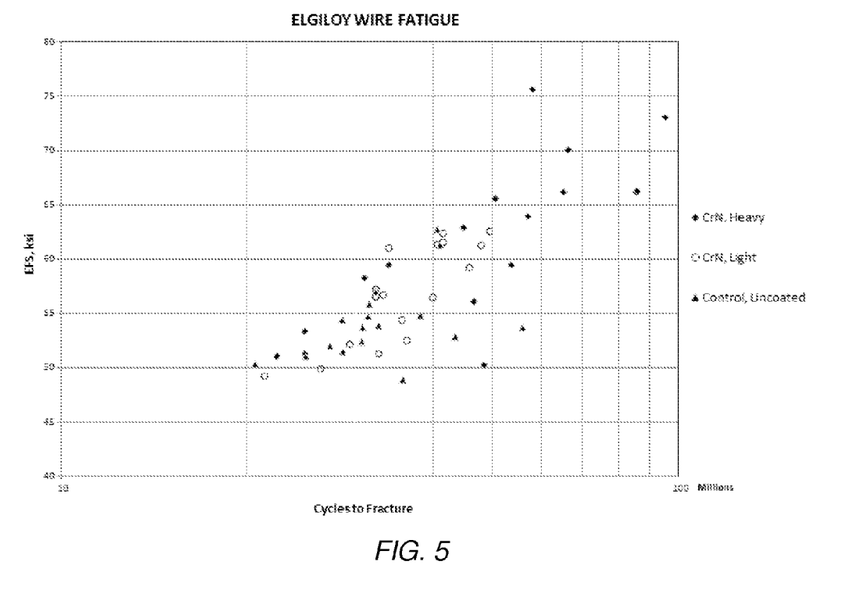
FIG. 5 shows the fatigue test results for heavy/light coated CrN wires and control uncoated wires as a function of kilopound per square inch (ksi) and number of stress cycles.

A bond layer of chromium was deposited onto Elgiloy® cobalt-chromium wires by LTAVD under argon. After depositing a thin layer of chromium (a few Angstroms thick), nitrogen gas was introduced into the reaction chamber to deposit a coating layer of CrN at a rate of 0.7-1 µm/hr. The temperature was kept below 150° C. (300° F.) throughout the process. In a heavy-coated set of wires, a 1.4-2 µm thick coating layer of CrN was deposited over the chromium bond layer. In a light-coated set of wires, the CrN coating layer was about 0.7 µm thick. FIG. 5 is a graph of fatigue test results of the heavy-coated wires, the light-coated wires, and a control group of uncoated wires. Each of the wires was subjected to 10 million cycles at a fixed mean stress and amplitude. If the wire did not fracture, the stress amplitude was increased and the wire was subjected to an additional 10 million cycles. The stress amplitude was further increased after each set of 10 million cycles until the wire fractured. As demonstrated in FIG. 5, the uncoated wires fractured at a lower number of cycles and at lower stress amplitudes as compared to the coated wires, with the CrN heavy-coated wires generally fracturing after a higher number of cycles and at higher stress amplitudes than the CrN light-coated wires.

The invention described and claimed herein is not to be limited in scope by the specific embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. A method for manufacturing a prosthetic heart valve to improve the fatigue life of a metal frame thereof, the method comprising:
   disposing a bond layer over at least a portion of a metal frame of a prosthetic heart valve, the bond layer comprising at least one elemental metal;
   vacuum depositing a coating layer over at least a portion of the bond layer, the coating layer comprising at least one of a metal oxide, a metal nitride, or a metal carbide; and
   securing a plurality of leaflets to the metal frame, the plurality of leaflets defining a one-way valve for blood flow therethrough.

2. The method of claim 1, wherein disposing the bond layer comprises disposing a bond layer by at least one of vacuum deposition or by electrochemical deposition.

3. The method of claim 1, wherein the at least one elemental metal is selected from the group consisting of aluminum, titanium, zirconium, hafnium, vanadium, niobium, tantalum, chromium, molybdenum, tungsten, ruthenium, cobalt, rhenium, iridium, palladium, platinum, copper, silver, and gold.

4. The method of claim 1, wherein disposing the bond layer over at least the portion of the metal frame comprises disposing the bond layer over at least a portion of at least one of a stent or a wireform of a heart valve.

5. The method of claim 1, wherein disposing the bond layer over at least the portion of the metal frame comprises disposing the bond layer over at least a portion of a metal frame comprising at least one of stainless steel, cobalt-chromium, titanium alloy, nitinol, a metal alloy, a shape-memory metal, or a super-elastic metal.

6. The method of claim 1, wherein vacuum depositing the coating layer comprises vacuum depositing a coating layer using at least one of physical vapor deposition (PVD), chemical vapor deposition (CVD), or low-temperature arc-vapor deposition (LTAVD).

7. The method of claim 1, wherein vacuum depositing the coating layer comprises vacuum depositing the coating layer at a temperature of about 150° C. (about 300° F.) or lower.

8. The method of claim 1, wherein vacuum depositing the coating layer comprises vacuum depositing a coating layer with a thickness of about 10 μm or less.

9. The method of claim 1, wherein the at least one of the metal oxide, the metal nitride, or the metal carbide of the coating layer comprises at least one metal selected from the group consisting of aluminum, titanium, zirconium, hafnium, vanadium, niobium, tantalum, chromium, molybdenum, tungsten, ruthenium, cobalt, rhenium, iridium, palladium, and platinum.

10. The method of claim 1, wherein vacuum depositing the coating layer comprises vacuum depositing a coating layer comprising chromium nitride.

11. The method of claim 1, wherein the bond layer and the coating layer include the same metal.

12. The method of claim 1, wherein the at least one elemental is selected from the group consisting of one or more noble metals.

13. The method of claim 1, wherein the coating layer has a grain size of about 20 nm or less.

14. The method of claim 1, wherein the coating layer includes both cubic and orthorhombic phases.

15. The method of claim 1, wherein the bond layer is chromium and the coating material is chromium nitride (CrN).

16. A method for manufacturing a prosthetic heart valve to improve the fatigue life of a metal frame thereof, the method comprising:

disposing a bond layer over at least a portion of a metal frame of a prosthetic heart valve, the bond layer including one or more stable and non-reactive elemental noble metals;

vacuum depositing a coating layer over at least a portion of the bond layer; and securing a plurality of leaflets to the metal frame, the plurality of leaflets defining a one-way valve for blood flow therethrough.

17. The method of claim 16, wherein vacuum depositing the coating layer comprises vacuum depositing the coating layer using at least one of physical vapor deposition (PVD), chemical vapor deposition (CVD), or low-temperature arc-vapor deposition (LTAVD).

18. The method of claim 16, wherein vacuum depositing the coating layer comprises vacuum depositing a coating layer comprising at least one of a metal oxide, a metal nitride, or a metal carbide.

19. The method of claim 16, wherein the bond layer comprises a combination of at least two stable and non-reactive elemental noble metals.

20. The method of claim 16, wherein disposing the bond layer comprising at least one of vacuum depositing a bond layer or electrochemically depositing a bond layer.

21. The method of claim 16, wherein securing the plurality of leaflets comprises securing a plurality of tissue leaflets.

22. The method of claim 16, wherein the noble metals are selected from the group consisting of ruthenium, palladium, silver, iridium, platinum, and gold.

23. The method of claim 16, wherein the coating layer has a grain size of about 20 nm or less.

24. The method of claim 16, wherein the coating layer includes both cubic and orthorhombic phases.

25. The method of claim 16, wherein the bond layer is chromium and the coating material is chromium nitride (CrN).

* * * * *